United States Patent
Cordo

(10) Patent No.: US 7,563,234 B2
(45) Date of Patent: Jul. 21, 2009

(54) ELECTROMYOGRAPHIC (EMG) FEEDBACK DURING AMES TREATMENT OF INDIVIDUALS WITH SEVERE NEUROMUSCULAR DEFICITS

(75) Inventor: Paul J. Cordo, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 195 days.

(21) Appl. No.: 11/487,095

(22) Filed: Jul. 13, 2006

(65) Prior Publication Data

US 2006/0253052 A1 Nov. 9, 2006

Related U.S. Application Data

(63) Continuation-in-part of application No. 11/105,189, filed on Apr. 11, 2005, which is a continuation of application No. 10/062,742, filed on Jan. 29, 2002, now Pat. No. 6,878,122.

(51) Int. Cl.
*A61H 1/00* (2006.01)

(52) U.S. Cl. .............................. 601/5; 601/33; 600/595

(58) Field of Classification Search ...................... 601/5, 601/23, 24, 26, 32, 34, 35, 36; 482/8, 9; 600/595; 607/49
See application file for complete search history.

(56) References Cited

U.S. PATENT DOCUMENTS

| | | | | | |
|---|---|---|---|---|---|
| 3,713,438 | A | * | 1/1973 | Knutsen | 601/35 |
| 4,479,646 | A | * | 10/1984 | Beistegui Chirapozu | 482/62 |
| 4,548,406 | A | * | 10/1985 | Beistegui Chirapozu | 482/62 |
| 4,570,927 | A | * | 2/1986 | Petrofsky et al. | 482/60 |
| 4,653,479 | A | * | 3/1987 | Maurer | 601/34 |
| 5,331,851 | A | * | 7/1994 | Parviainen et al. | 73/379.01 |
| 5,980,435 | A | * | 11/1999 | Joutras et al. | 482/114 |
| 6,077,201 | A | * | 6/2000 | Cheng | 482/57 |

* cited by examiner

*Primary Examiner*—Danton DeMille
(74) *Attorney, Agent, or Firm*—Stoel Rives LLP

(57) ABSTRACT

A method of rehabilitating a patient suffering partial or total loss of motor control of an appendicular joint caused by injury or neurological disorder but exhibiting clinically plegic (i.e., paralyzed) muscles and retaining minimal ability to weakly contract the muscles develops overt movement at a joint and ultimately leads to improved functionality. The method entails use of feedback in which the patient views and/or hears a signal related to the intensity of electromyographic (EMG) activity the patient produces in the appropriate muscles while attempting to move the paretic or plegic joint. The method is intended as an alternative form of feedback for highly disabled patients while they receive therapy using an Assisted Movement with Enhanced Sensation (AMES) device providing joint torque feedback.

7 Claims, 3 Drawing Sheets

ELECTROMYOGRAPHIC (EMG) FEEDBACK DURING AMES TREATMENT OF INDIVIDUALS WITH SEVERE NEUROMUSCULAR DEFICITS

RELATED APPLICATIONS

This is a continuation-in-part of U.S. patent application Ser. No. 11/105,189, filed Apr. 11, 2005, which is a continuation of U.S. patent application Ser. No. 10/062,742, filed Jan. 29, 2002, now U.S. Pat. No. 6,878,122.

COPYRIGHT NOTICE

© 2006 Oregon Health & Science University. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71 (d).

TECHNICAL FIELD

The invention pertains to the use of therapy termed "AMES," or Assisted Movement with Enhanced Sensation, of a type described in U.S. Pat. No. 6,878,122 in the rehabilitation of patients suffering from stroke, traumatic brain injury, and other neuromuscular disorders such as cerebral palsy and spinal cord injury and, in particular, to the use of AMES therapy on a sub-population of such patients who are unable to generate movement in one or both directions at a joint, such as the wrist or ankle.

BACKGROUND INFORMATION

In the United States, stroke-related illness is the leading cause of long-term disability. Each year approximately 750,000 individuals in this country suffer a stroke, and for those who survive, a majority will be afflicted with a motor disability. There are currently 4.5 million U.S. citizens permanently disabled by stroke, with annual health-care costs of approximately $50 billion.

Neuromuscular symptoms of stroke include, but are not limited to, muscular paresis (i.e., reduced ability to activate muscles), plegia (i.e., complete paralysis of muscles), and dyssynergia (i.e., inability to activate certain muscles without inadvertent activation of inappropriate muscles in the same limb or other limbs). Often a stroke patient will be plegic at a joint for attempted movement in one direction and paretic in the other direction.

The diagnosis of plegia in stroke victims does not necessarily mean that the individual is completely incapable of activating the appropriate muscles at a joint. Rather, in many cases, the absence of movement is a result of insufficient levels of muscle activation and joint torque to achieve overt movement. Moreover, movement at a joint may be prevented by inadvertent, concomitant activation of the muscles on the wrong side of the joint (i.e., dyssynergia), whereby inadvertent activation overpowers weak activation of muscles on the appropriate side of the joint.

In certain embodiments of AMES therapy described in U.S. Pat. No. 6,878,122, which is assigned to the assignee of this patent application, patients with neuromuscular disorders receive feedback in the form of joint torque. The patients are fed back the amount of torque they are able to produce voluntarily while assisting joint motion produced by a motorized robotic device. If the patient is incapable of producing joint torque during AMES treatment, the patient receives no feedback, even if the patient's attempts to assist movement produce appropriate, but weak, activation of the appropriate muscles. Without useful feedback, these weak, but not completely paralyzed, patients are less likely to benefit from treatment.

SUMMARY OF THE DISCLOSURE

Preferred embodiments entail use of electromyographic (EMG) feedback of the electrical activity from muscles so that certain neuromuscular disorder-afflicted patients who are incapable of exerting overt torque at a joint can, during AMES treatment, receive feedback that is related to volitional muscle activation. These weak but not completely paralyzed patients can, therefore, benefit from AMES treatment.

Such use of EMG feedback expands the patient population benefiting from AMES treatment to include individuals who are capable of activating muscles voluntarily at a joint, but to a degree that is too weak to produce overt joint torque and movement.

Preferred embodiments of the invention use EMG feedback with AMES treatment to allow a patient who superficially appears to be totally paralyzed at a joint (i.e., in one or more directions) to recover to a point at which the patient can produce overt joint torque and movement. After the patient has regained some significant amount of voluntary movement, the patient may be shifted to treatment with joint torque feedback.

In addition to stroke, cerebral palsy (CP), traumatic brain injury (TBI), and incomplete spinal cord injury (iSCI) are three of several neuromuscular disorders in which apparent plegia can be produced, but in which the patient is actually capable of weakly activating the muscles crossing a joint. These non-stroke patients with apparent, but not actual, plegia may respond to rehabilitation if EMG feedback is employed in conjunction with AMES treatment.

Additional aspects and advantages will be apparent from the following detailed description of preferred embodiments, which proceeds with reference to the accompanying drawings.

DETAILED DESCRIPTION OF PREFERRED EMBODIMENTS

AMES therapy is preferably practiced with use of a joint-ranging device that rotates the joint of a patient with concomitant vibration of lengthening muscles associated with the joint while the patient attempts to assist the joint rotation with voluntary contraction of corresponding muscles associated with the joint. A preferred joint-ranging device is an AMES rehabilitation device described in U.S. Pat. No. 6,878,122.

Figure 1:
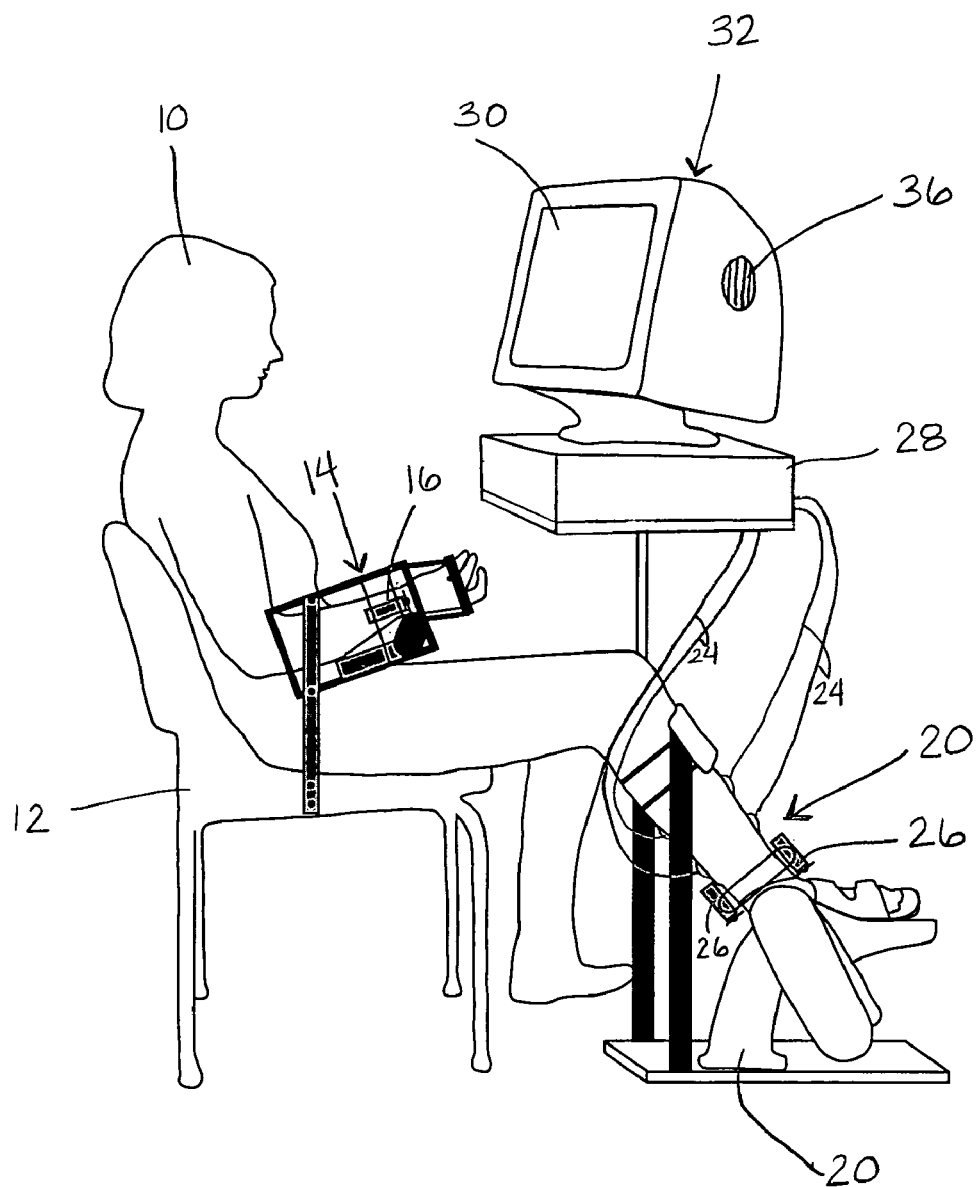
FIG. 1 is a pictorial view of a patient in position to be treated with AMES therapy while using visual feedback, auditory feedback, or both.

FIG. 1 shows a patient 10 sitting in a chair 12 supporting a wrist joint-ranging device 14 affixed to the patient's right forearm. Wrist joint-ranging device 14 is powered to rotate the wrist joint alternately in flexion and to extension directions. Two vibrators 16 (only one shown in FIG. 1) apply during wrist joint rotation concomitant vibration (e.g., 40 Hz-80 Hz) of lengthening muscles associated with the wrist joint while patient 10 attempts to assist the wrist joint rotation with voluntary contraction of corresponding shortening muscles associated with the wrist joint. FIG. 1 also shows patient 10 with her right lower leg secured in a foot joint-ranging device 20 affixed to the patient's shoe and to the calf just below the knee. Foot joint-ranging device 20 is powered to rotate the ankle joint alternately in flexion and to extension directions. Two vibrators 26 apply during ankle joint rotation concomitant vibration of lengthening muscles associated with the ankle joint while patient 10 attempts to assist the ankle joint rotation with voluntary contraction of corresponding shortening muscles associated with the ankle joint.

For operation of either wrist joint-ranging device 14 or foot joint-ranging device 20, an EMG signal is typically acquired (i.e., recorded) from a patient's muscle or muscles to which pairs of electrodes 24 are attached. The EMG signal represents the differential voltage between electrodes 24 of an electrode pair, referenced to a neutral voltage obtained from an inactive location of the patient's body. Each electrode 24 may be composed of a rounded metal protuberance, typically 0.5 cm-0.7 cm in diameter and depressing the skin 1 mm-3 mm. Electrodes 24 may be embedded within an enclosure for the arm or leg, such as in an AMES rehabilitation device. Alternatively, EMG signals may be picked up by pairs of disposable electrodes 24 adhered to the patient's skin over the muscle or muscles of interest. Typically, pairs of EMG electrodes 24 are oriented parallel to the long dimension of a muscle and/or collinear to the orientation of muscle fibers within the muscle or muscles of interest. The EMG signals provide to patient 10 feedback information representing EMG activity of the lengthening and shortening muscles of interest. The feedback information identifies the degree to which patient 10 is able to assist joint rotation imparted by either wrist joint-ranging device 14 or foot joint-ranging device 20.

The EMG signal, typically 10 μV-2000 μV in amplitude, is delivered to an EMG instrument 28 for amplification prior to visualization or other usage. Amplification is typically carried out in two stages to minimize electrical noise, near the pick-up site (e.g., ×100) and near the usage site (e.g., ×20-×50), resulting in an amplified signal in the region of 1 V. At this stage of processing, the signal is termed "raw" EMG, is both positive- and negative-going, and has a spiky appearance (e.g., FIG. 2, line A).

To better utilize the raw EMG signal, further processing is usually carried out. Typically, the raw signal is rectified (i.e., the negative-going components are vertically flipped about 0 V to become positive-going) (e.g., FIG. 2, line B), and the rectified signal is then low-pass filtered to smooth it (e.g., FIG. 2, line C). This rectified, smoothed EMG signal can then be used to move a needle on a dial (not shown); to increment a number on a read-out (not shown); to move a graphic object 34 on a display screen 30 of a visual display monitor 32 (e.g., FIG. 3); or to modulate the intensity or frequency of a sound audible from a loudspeaker 36 in display monitor 32 (e.g., FIG. 1). Commercially available EMG instrumentation amplifier equipment suitable for practicing the above-described process is a Myosystem 2000, manufactured by Noraxon USA, Inc., Scottsdale, Ariz. The electrodes are conventional ECG stick-on electrodes.

Figure 2:
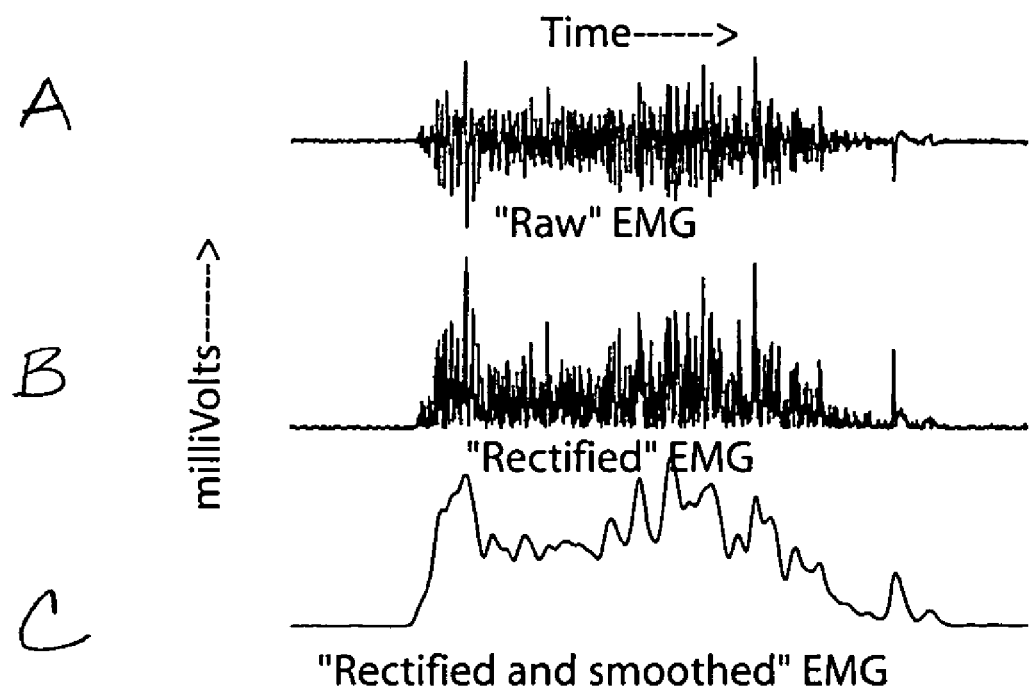
FIG. 2 is a diagrammatic representation of, respectively, raw (i.e., unprocessed) EMG, rectified EMG, and rectified and low-pass filtered EMG waveform traces developed during voluntary movement of an appendicular joint of a patient.
Figure 3:
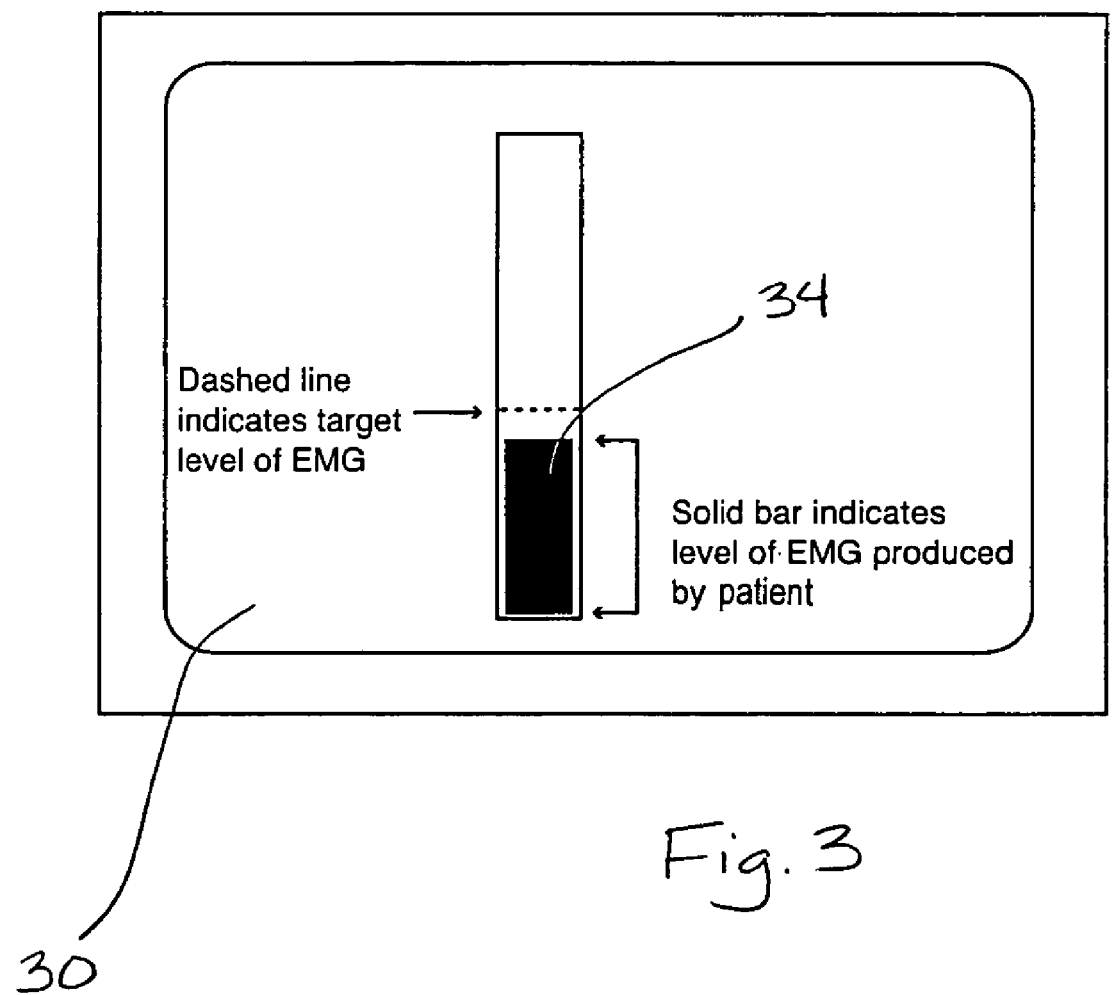
FIG. 3 is a diagrammatic representation of a simple visually presented embodiment of EMG feedback.

In a first preferred embodiment, the rectified, low-pass filtered EMG signal is used to move graphics object 34 (e.g., FIG. 3) on display screen 30 of display monitor 32. In the example shown in FIG. 3, the height of a bar 34 represents the instantaneous amplitude of the processed EMG signal (FIG. 2, line C).

In a second preferred embodiment, the rectified, low-pass filtered EMG signal is used to control the intensity, frequency, or both, of a tone or a recorded message played over loudspeaker 36 or headphones (not shown).

In a third preferred embodiment, the rectified, low-pass filtered EMG signal is used to control both visual feedback and auditory feedback, which are simultaneously presented in a goal-directed virtual-reality (i.e., video) game displayed on display screen 30.

EXAMPLE 1

A 34 year-old female, 4 years post-stroke, with severe paresis and joint rigidity in her right wrist and fingers, was treated in accordance with the standard AMES therapy using joint torque feedback. Her wrist and fingers were paretic and spastic in the flexion direction and clinically plegic in the extensor direction. After 11 weeks of the standard AMES therapy, her flexion strength increased by 600%. In contrast, her extension strength changed from zero to negative values, that is, when she attempted to extend, she flexed. Closer examination with EMG recording revealed that her wrist and finger extensor muscles were active when she attempted to extend, but that inadvertent activation of the recently strengthened wrist and finger flexor muscles overpowered the extensor muscles. To correct such muscle dyscoordination, the patient was then provided EMG feedback for a total of 8 hours of therapy, after which she was better able to differentially activate the flexors and extensors of the wrist and fingers. She then returned to the standard AMES therapy using joint torque feedback. Three months later, her extensor torque had reversed from negative to positive and equaled the torque in her flexor muscles. The patient's use of EMG feedback information enabled the patient to retrain her brain through therapy to produce coordinated, individuated activity of the flexor and extensor muscles of her wrist and fingers.

EXAMPLE 2

A 44 year-old male, 3 years post-stroke, with severe paresis in his left wrist and fingers, was treated in accordance with the standard AMES therapy using joint torque feedback. His wrist and fingers were paretic in the flexion direction and clinically plegic in the extensor direction. Closer examination revealed a low level of EMG activity in the extensor muscles during attempted extension, but the activity was too weak to produce overt movement of the wrist and fingers. Prior to using the standard AMES device with joint torque feedback, the patient was provided EMG feedback for a total of 6 hours of therapy, after which he was able to generate extension torque and movement of the wrist and fingers. The feedback he received during AMES therapy was then changed from EMG to torque, and he began partial recovery of upper limb use.

It will be obvious to those having skill in the art that many changes may be made to the details of the above-described embodiments without departing from the underlying principles of the invention. The scope of the present invention should, therefore, be determined only by the following claims.

The invention claimed is:

1. A method of rehabilitating a patient experiencing skeletal joint motor control loss resulting from neurological disorders, the rehabilitation entailing retraining the patient's brain to produce coordinated, individuated muscle activity, comprising:

practicing assisted movement with enhanced sensation (AMES), in which a joint-ranging device rotates a joint of the patient with concomitant vibration of lengthening muscles associated with the joint while the patient attempts to assist the rotation of the joint with voluntary contraction of corresponding shortening muscles associated with the joint; and providing to the patient feedback information indicative of electromyographic (EMG) activity of the lengthening and shortening muscles, the feedback information including information indicating which ones of the lengthening and shortening muscles are appropriate for the patient to activate as the patient assists joint rotation imparted by the joint-ranging device to correct muscle dyscoordination and thereby produce coordinated, individuated muscle activity.

2. The method of claim 1, in which the patient is incapable of producing visible voluntary joint movement or torque in one or more directions but is capable of generating measurable EMG in the corresponding lengthening and shortening muscles during attempted movement.

3. The method of claim 1, in which the EMG signal provided during attempted voluntary movement is processed to quantify the EMG signal amplitude.

4. The method of claim 3, in which in which the processed EMG signal of the attempted voluntary movement is fed back to the patient to identify a degree of the patient's success in the attempting of voluntarily contraction of the shortening muscles.

5. The method of claim 1, in which the feedback information of EMG activity is visual, presented by moving a graphic object on a display screen, moving the needle of a dial, or incrementing a number on a read-out.

6. The method of claim 1, in which the EMG feedback information is auditory, presented as a change in the frequency or intensity of a tone, or as a recorded message over loudspeakers or headphones.

7. The method of claim 1, in which the EMG feedback information is presented as a visual cue, an auditory cue, or both, by a goal-directed virtual reality or video game.

* * * * *

UNITED STATES PATENT AND TRADEMARK OFFICE
CERTIFICATE OF CORRECTION

| | | |
|---|---|---|
| PATENT NO. | : 7,563,234 B2 | Page 1 of 1 |
| APPLICATION NO. | : 11/487095 | |
| DATED | : July 21, 2009 | |
| INVENTOR(S) | : Paul J. Cordo | |

It is certified that error appears in the above-identified patent and that said Letters Patent is hereby corrected as shown below:

In the Specification

At Column 1, Line 12, between the paragraph of headed with "RELATED APPLICATIONS" and the heading "COPYRIGHT NOTICE", please insert the following heading and paragraph:

-- GOVERNMENT SUPPORT
This invention was made with government support under R01 AR031017 and R43 NS060192 awarded by the National Institutes of Health. The government has certain rights in the invention. --

Signed and Sealed this
Sixth Day of August, 2019

Andrei Iancu
*Director of the United States Patent and Trademark Office*